US010799252B2

(12) United States Patent
Libby et al.

(10) Patent No.: US 10,799,252 B2
(45) Date of Patent: Oct. 13, 2020

(54) PROXIMAL BICEPS TENODESIS WITH BICEPS BUTTON

(71) Applicant: ARTHREX, INC., Naples, FL (US)

(72) Inventors: Dustin T. Libby, Naples, FL (US); William C. Benavitz, Naples, FL (US); Thomas Dooney, Jr., Naples, FL (US); Harri Helio, Helsinki (FI); James J. Guerra, Naples, FL (US)

(73) Assignee: ARTHREX, INC., Naples, FL (US)

( * ) Notice: Subject to any disclaimer, the term of this patent is extended or adjusted under 35 U.S.C. 154(b) by 94 days.

(21) Appl. No.: 16/241,053

(22) Filed: Jan. 7, 2019

(65) Prior Publication Data

US 2019/0133610 A1 May 9, 2019

Related U.S. Application Data

(63) Continuation of application No. 14/610,451, filed on Jan. 30, 2015, now Pat. No. 10,206,694.

(60) Provisional application No. 61/934,270, filed on Jan. 31, 2014.

(51) Int. Cl.
*A61B 17/17* (2006.01)
*A61F 2/08* (2006.01)
*A61B 17/04* (2006.01)

(52) U.S. Cl.
CPC ........ *A61B 17/1714* (2013.01); *A61F 2/0805* (2013.01); *A61F 2/0811* (2013.01); *A61B 17/1778* (2016.11); *A61B 2017/0404* (2013.01); *A61F 2002/0852* (2013.01)

(58) Field of Classification Search
CPC . A61B 17/0401; A61B 17/17; A61B 17/1714; A61B 17/1778; A61B 2017/0404; A61F 2/0805; A61F 2/0811; A61F 2002/0847; A61F 2002/0852
See application file for complete search history.

(56) References Cited

U.S. PATENT DOCUMENTS

| 5,330,468 | A | * | 7/1994 | Burkhart | A61B 17/1796 606/96 |
| 5,688,284 | A | * | 11/1997 | Chervitz | A61B 17/1714 606/102 |
| 6,398,812 | B1 | * | 6/2002 | Masini | A61F 2/4059 623/19.11 |
| 7,569,059 | B2 | * | 8/2009 | Cerundolo | A61B 17/0401 606/86 R |
| 7,771,441 | B2 | * | 8/2010 | Cerundolo | A61B 17/0401 606/148 |
| 7,833,230 | B2 | * | 11/2010 | Cerundolo | A61B 17/0401 606/228 |
| 8,361,079 | B2 | * | 1/2013 | Pandya | A61B 17/1778 606/80 |
| 9,113,977 | B2 | * | 8/2015 | Euteneuer | A61F 2/0063 |
| 9,730,708 | B2 | * | 8/2017 | Fitzpatrick | A61B 17/1684 |

(Continued)

*Primary Examiner* — Eric S Gibson
(74) *Attorney, Agent, or Firm* — Carlson, Gaskey & Olds

(57) ABSTRACT

Methods and drill guide systems that provide internalization of the biceps tendon with use of fixation devices such as the Arthrex BicepsButton™ or Pectoralis Button tensioned outside a smaller converged drill hole. The technique converges two angled drill holes and use the button to fixate a reinforced (whipstitched) biceps tendon into a single bone versus stabilizing two bones. The biceps tendon is being pulled into the larger of the drilled holes and fixed by the button outside of the smaller drilled hole.

20 Claims, 17 Drawing Sheets

(56) References Cited

U.S. PATENT DOCUMENTS

| | | | |
|---|---|---|---|
| 10,206,694 B2* | 2/2019 | Libby | A61B 17/1714 |
| 2003/0050666 A1 | 3/2003 | Grafton | |
| 2004/0049195 A1* | 3/2004 | Singhatat | A61F 2/0811 |
| | | | 606/98 |
| 2004/0172034 A1* | 9/2004 | Re | A61B 17/1764 |
| | | | 606/329 |
| 2005/0192631 A1 | 9/2005 | Grafton | |
| 2006/0241657 A1* | 10/2006 | Cerundolo | A61B 17/0401 |
| | | | 606/148 |
| 2006/0259076 A1 | 11/2006 | Burkhart et al. | |
| 2007/0135843 A1* | 6/2007 | Burkhart | A61B 17/06166 |
| | | | 606/232 |
| 2009/0054928 A1* | 2/2009 | Denham | A61B 17/0401 |
| | | | 606/232 |
| 2009/0082805 A1* | 3/2009 | Kaiser | A61B 17/06166 |
| | | | 606/228 |
| 2009/0105754 A1 | 4/2009 | Sethi | |
| 2009/0149884 A1* | 6/2009 | Snyder | A61F 2/0805 |
| | | | 606/233 |
| 2010/0152752 A1* | 6/2010 | Denove | A61B 17/0469 |
| | | | 606/148 |
| 2010/0228254 A1* | 9/2010 | Pandya | A61B 17/1684 |
| | | | 606/80 |
| 2010/0256677 A1* | 10/2010 | Albertorio | A61F 2/0811 |
| | | | 606/232 |
| 2011/0087326 A1* | 4/2011 | Paulos | A61B 17/0401 |
| | | | 623/13.14 |
| 2012/0065732 A1* | 3/2012 | Roller | A61F 2/0811 |
| | | | 623/13.14 |
| 2012/0123474 A1* | 5/2012 | Zajac | A61B 17/86 |
| | | | 606/232 |
| 2013/0123842 A1* | 5/2013 | Chan | A61B 17/0401 |
| | | | 606/232 |
| 2013/0123843 A1* | 5/2013 | Chan | A61B 17/0401 |
| | | | 606/232 |
| 2014/0257314 A1* | 9/2014 | Brown | A61B 17/0401 |
| | | | 606/98 |
| 2015/0216522 A1* | 8/2015 | Ticker | A61B 17/0401 |
| | | | 606/232 |
| 2015/0216542 A1* | 8/2015 | Libby | A61B 17/1714 |
| | | | 606/96 |
| 2015/0297211 A1* | 10/2015 | Sullivan | A61B 17/0401 |
| | | | 606/232 |
| 2016/0166297 A1* | 6/2016 | Mighell | A61B 17/80 |
| | | | 606/291 |
| 2016/0213370 A1* | 7/2016 | Chan | A61B 17/0401 |
| 2016/0228118 A1* | 8/2016 | Chan | A61B 17/0401 |
| 2017/0112511 A1* | 4/2017 | Fallin | A61F 2/0811 |
| 2019/0133610 A1* | 5/2019 | Libby | A61B 17/0401 |

\* cited by examiner

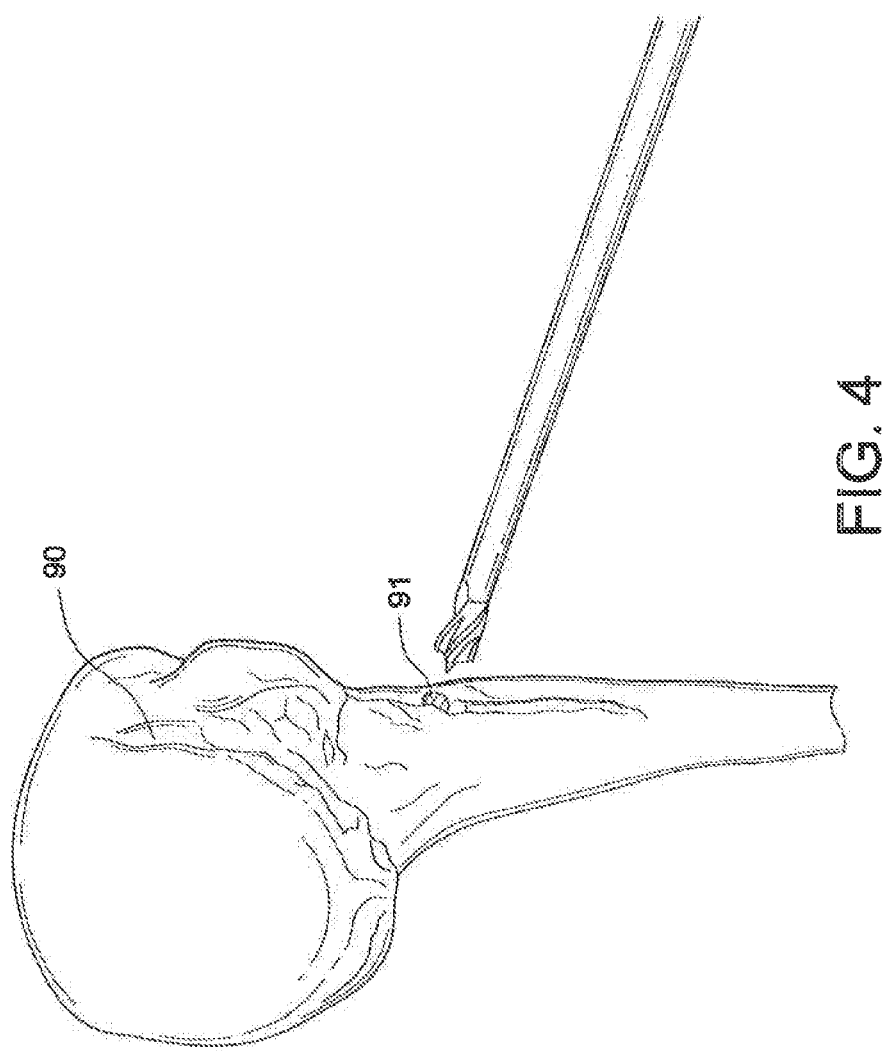

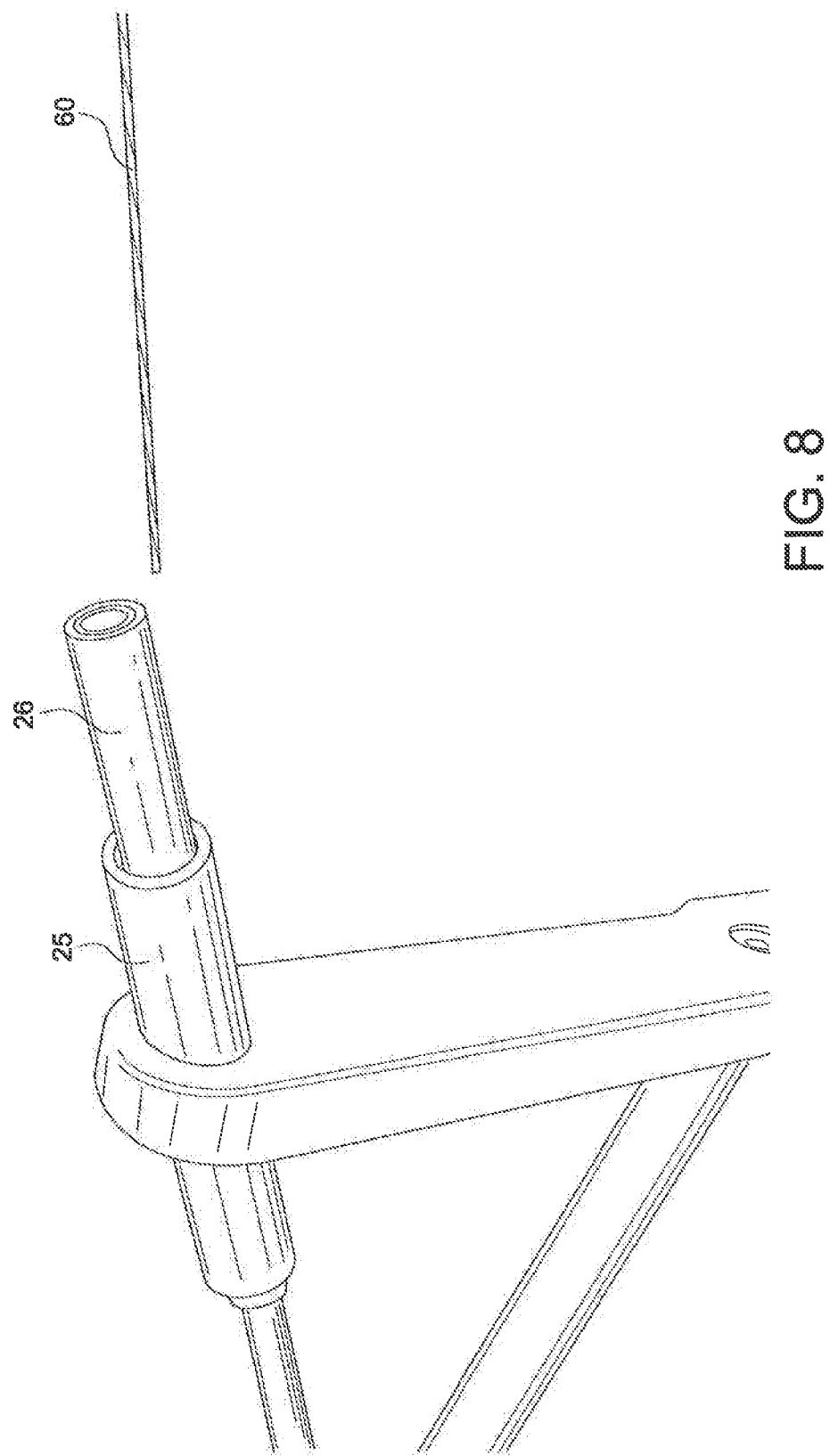

PROXIMAL BICEPS TENODESIS WITH BICEPS BUTTON

CROSS-REFERENCE TO RELATED APPLICATIONS

This is a continuation of U.S. patent application Ser. No. 14/610,451, filed Jan. 30, 2015, which claims the benefit of U.S. Provisional Application No. 61/934,270, filed Jan. 31, 2014, the entire disclosures of which are incorporated by reference herein.

FIELD OF THE INVENTION

The present invention relates to the field of surgery and, more specifically, to tendon repairs for reconstructive surgeries.

BACKGROUND OF THE INVENTION

A common type of biceps tendon tear is detachment (partial or complete) of one of the biceps tendons within the shoulder joint. There are two attachments of the biceps tendon at the shoulder, one within the shoulder joint (the long head of the biceps) and the other in front of the shoulder joint (the short head of the biceps). Injuries to the proximal biceps tendon almost always involve the long head of the biceps. When the long head of the biceps tendon is damaged, a treatment that may be considered is biceps tenodesis.

A biceps tenodesis procedure involves cutting the long head of the biceps just prior to its insertion on the superior labrum and then anchoring the tendon along its anatomical course more distally along the humerus. A number of different anchoring techniques are currently used by surgeons. These techniques include fixation devices such as cortical buttons, Bio-Tenodesis screws and suture anchors. The key to performing a biceps tenodesis is moving the tendon from its normal attachment within the shoulder joint to a new location further down the humerus. An optimal technique would be characterized by limited anterior incisions, early range of motion due to strength and gapping of the repair, and minimum complications.

There is a need for improved methods of attachment of the biceps tendon outside of the shoulder joint that can cause fewer problems within the joint. Also needed are methods and devices that allow internalization of the biceps tendon with use of fixation devices (such as cortical buttons) that are tensioned outside a smaller converged drill hole.

SUMMARY OF THE INVENTION

The method of the present invention provides internalization of the biceps tendon with use of fixation devices such as the Arthrex BicepsButton™ or Pectoralis Button tensioned outside a smaller converged drill hole. The technique converges two angled drill holes and use the button to fixate a reinforced (whipstitched) biceps tendon into a single bone versus stabilizing two bones. The biceps tendon is being pulled into the larger of the drilled holes and fixed by the button outside of the smaller drilled hole.

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 4-19 illustrate subsequent steps of a method of proximal biceps tenodesis of the present invention with the drill guide system of FIG. 1 (biceps tenodesis with outrigger and button).

DETAILED DESCRIPTION OF THE PREFERRED EMBODIMENTS

Figure 1:
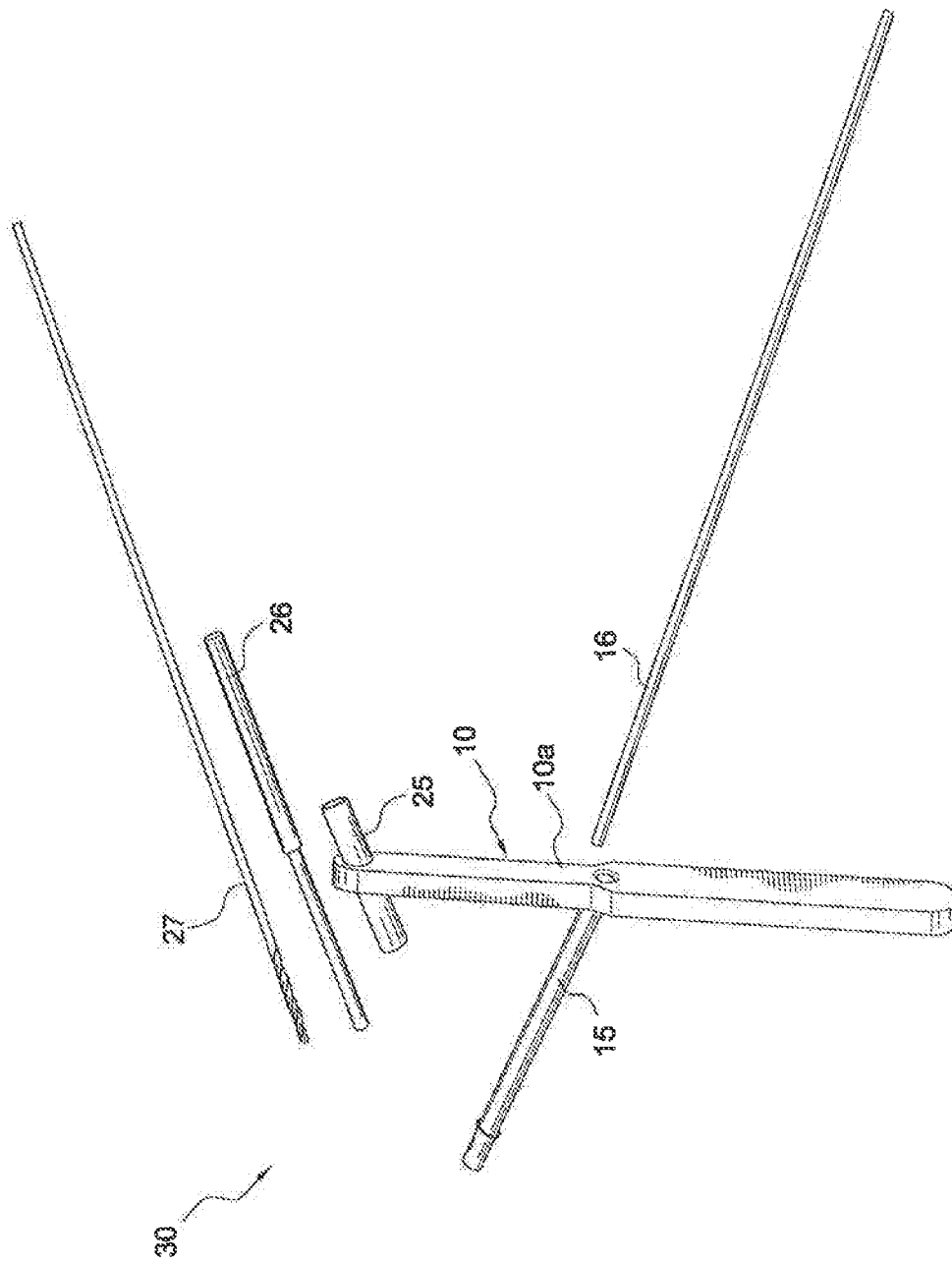
FIGS. 1-3 illustrate various views of a drill guide system used in the method of proximal biceps tenodesis of the present invention.

In the following detailed description, reference is made to various specific embodiments in which the invention may be practiced. These embodiments are described with sufficient detail to enable those skilled in the art to practice the invention, and it is to be understood that other embodiments may be employed, and that structural changes may be made without departing from the scope of the present invention.

The technique of the present invention improves the biomechanics of the overall repair and helps overcome surgeons' concerns about rapid return to ADLs. The technique reliably seats the tendon against the proximal cortex of the bone socket, maximizing the surface area for bone to tendon healing. The technique takes advantage of cortical fixation, while providing the unique advantage of minimizing gap formation. The proximal biceps tenodesis technique restores the anatomical footprint and provides the optimal strength and biomechanical characteristics to allow immediate active range of motion.

The technique converges two angled drill holes and use a fixation device (such as an exemplary biceps or pectoralis button) to fixate a reinforced biceps tendon (for example, a sutured or whipstitched biceps tendon) into a single bone versus stabilizing two bones. An exemplary BicepsButton™ is detailed and described, for example, in U.S. Patent Application Publication No. 2009/0105754, entitled "Tendon Repair Using Tendon-Slide Technique", the disclosure of which is incorporated in its entirety by reference herein. The biceps tendon is being pulled into the larger of the drilled holes and fixed by the pectoralis button outside of the smaller drilled hole.

The present invention provides a method of biceps tenodesis by inter alia the steps of: (i) exposing a biceps tendon attached to an extremity of a patient; (ii) providing a drill guide system comprising a triangular guide including a plate, a first cannulated tube and a second cannulated tube, the second cannulated tube being configured to allow a cannulated sleeve and drill to pass therethrough, the plate, the first cannulated tube and the second cannulated tube being integrally attached to each other and oriented in an overall triangular configuration; (iii) forming a first tunnel or socket; (iv) forming a second tunnel or socket in the humerus with the drill guide system, so that the second tunnel or socket is spaced apart from the first tunnel or socket and intersects the first tunnel to form a resulting humeral intersecting structure having a V-shaped configuration; (v) attaching at least one flexible strand to the biceps at a biceps region adjacent the first tunnel or socket; (vi) inserting the biceps in the first tunnel or socket; (vii) pulling the at least one flexible strand attached to the biceps through and out of the second tunnel or socket; and (viii) securing the at least one flexible strand with a fixation device (for example, a button) on a cortical surface of the humerus.

The present invention provides a method of arthroscopic biceps tenodesis by inter alia the steps of: (i) exposing a biceps tendon attached to an extremity of a patient; (ii) forming a unicortical bone socket (first socket) into proximal humerus on which the biceps tendon is attached, at the inferior border of the bicepital groove; (iii) inserting a first drill guide of a triangular guide into the unicortical bone socket; (iv) with the first drill guide remaining in place, forming a second tunnel or socket in the humerus with a second drill guide of the triangular guide, so that the second tunnel or socket is spaced apart from the first socket and intersects the first socket to form a resulting humeral intersecting structure, the first and second drill guides being non-parallel relative to each other, to allow the resulting humeral intersecting structure to have a V-shaped configuration; (v) attaching at least one flexible strand to the biceps tendon adjacent the first socket; (vi) loading the ends of the at least one flexible strand through a suture passing device (such as a FiberStick™ suture or nitinol loop, for example) and pulling the ends of the at least one flexible strand attached to the biceps through and out of the second tunnel or socket, to dock the biceps into the first socket; and (vii) securing the ends of the at least one flexible strand to the cortical bone surface by tying the ends on top of a BicepsButton™ or pectoralis button.

Figure 3:
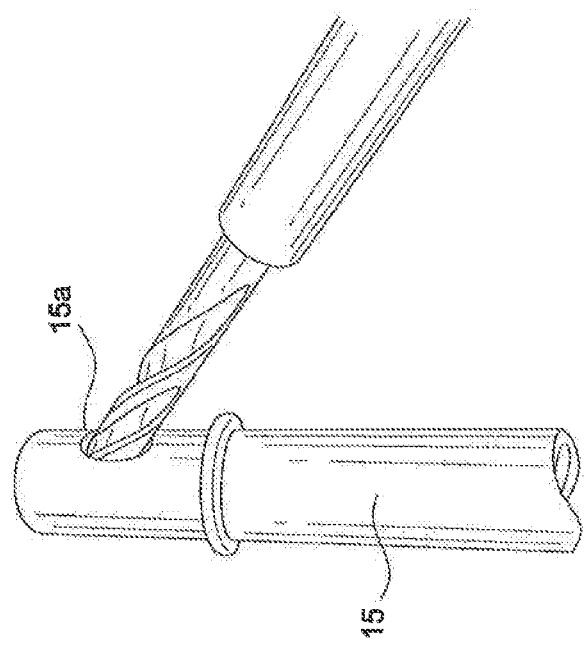
Figure 2:
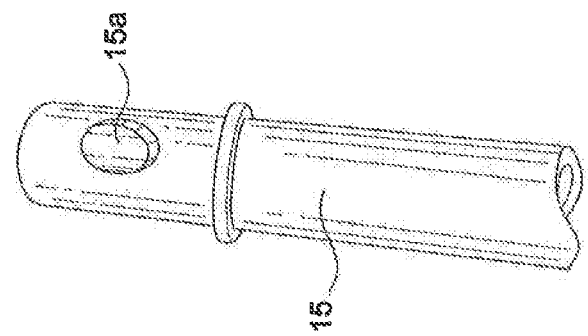
Figure 19:
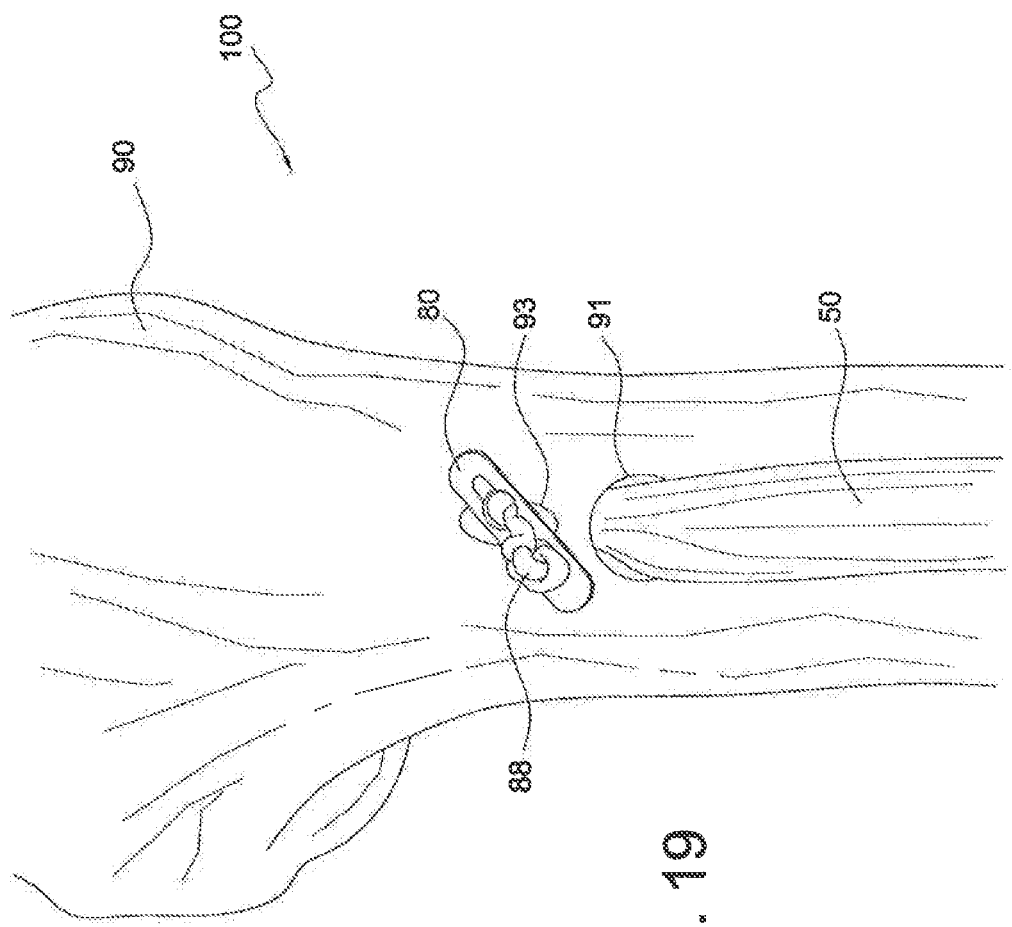

Referring now to the drawings, FIGS. 1-3 illustrate various views of a drill guide system 30 of the present invention used in a method of proximal biceps tenodesis to achieve final repair 100 (FIG. 19).

The system 30 includes a triangular guide 10 which includes a plate 10*a* with a cannulated tube 15 on the inferior portion and a cannulated tube 25 on the superior portion. System 30 also includes a cannulated sleeve 26 (adjacent to the superior cannulated tube 25) and a drill 27 configured to pass through the cannulated sleeve 26. System 30 also includes a solid rod 16 (adjacent to the inferior cannulated tube) designed to pass through the cannulated tube 15.

Inferior cannulated tube 15 (first drill guide 15 or drill guide #1) and superior cannulated tube 25 (second drill guide 25 or drill guide #2) are configured to be non-parallel to each other and to plate 10*a* so that, when viewed from the top, the plate 10*a*, inferior tube 15 and superior tube 25 form a triangular shape. Preferably, the angles of the triangular shape formed by the three structures are about 60 degrees.

As shown in FIGS. 2 and 3, the tip of the inferior cannulated tube 15 of the triangular guide 10 has a pilot hole 15*a* which provides for a drill stop and a method to capture a stiffened suture using the solid rod 16 (as detailed below).

An exemplary series of steps of a method of proximal biceps tenodesis of the present invention is set forth below. Although, for simplicity, the invention will be described with reference to biceps tendon, the invention is not limited to this exemplary only embodiment and has applicability to any type of native tendon.

FIG. 4: In an arthroscopic or open fashion, a unicortical socket 91 is formed in bone 90 (proximal humerus 90) at the desired level of the biceps tenodesis. Proximal humerus 90 is shown with bone socket 91 formed at the inferior border of the bicepital groove.

Figure 5:
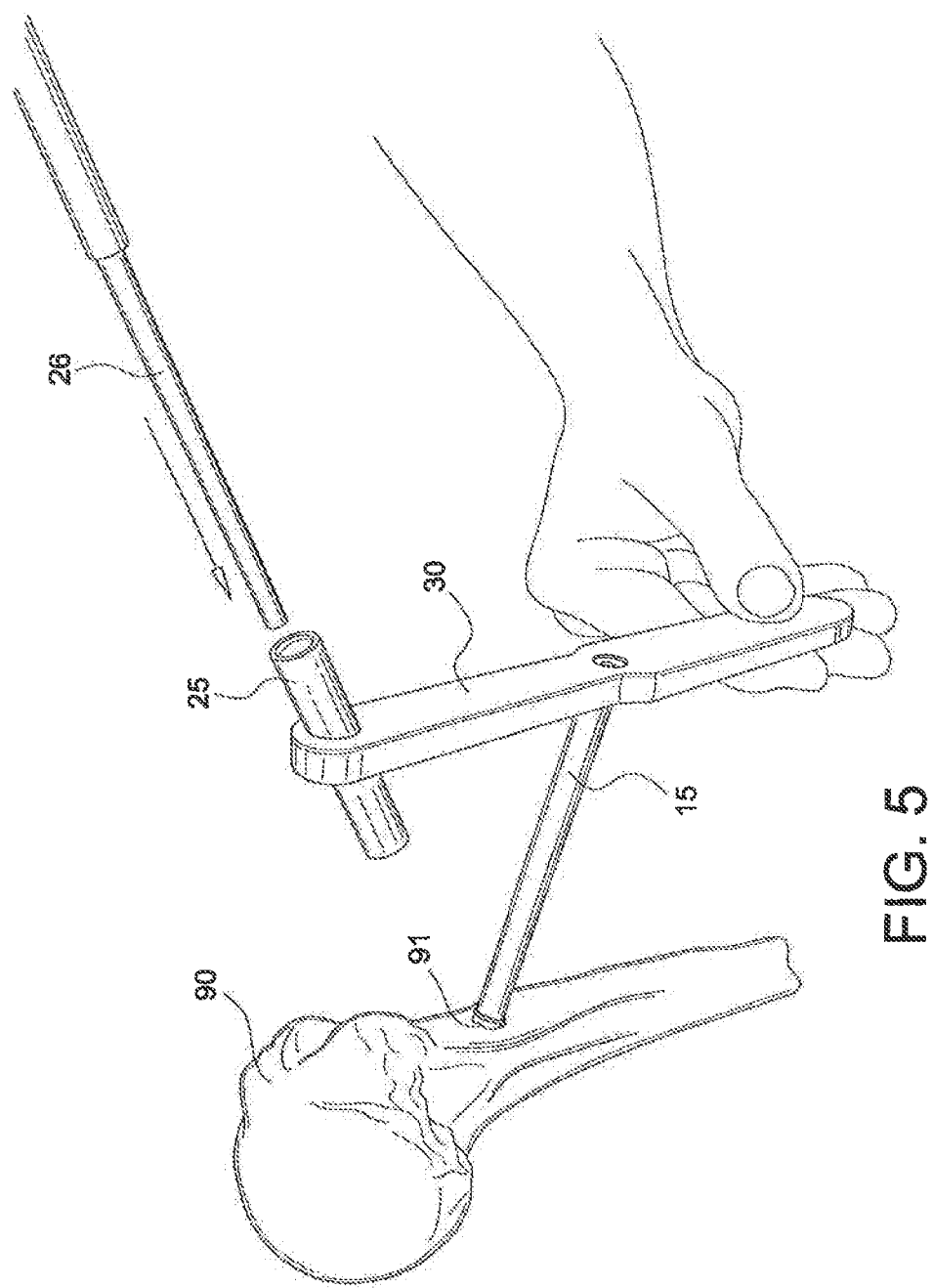

FIG. 5: The inferior cannulated tube end 15 is inserted into the previously formed bone socket 91 and the cannulated sleeve 26 is then inserted into the cannulated tube 25 on the superior portion of the triangular guide 10 as shown.

Figure 7:
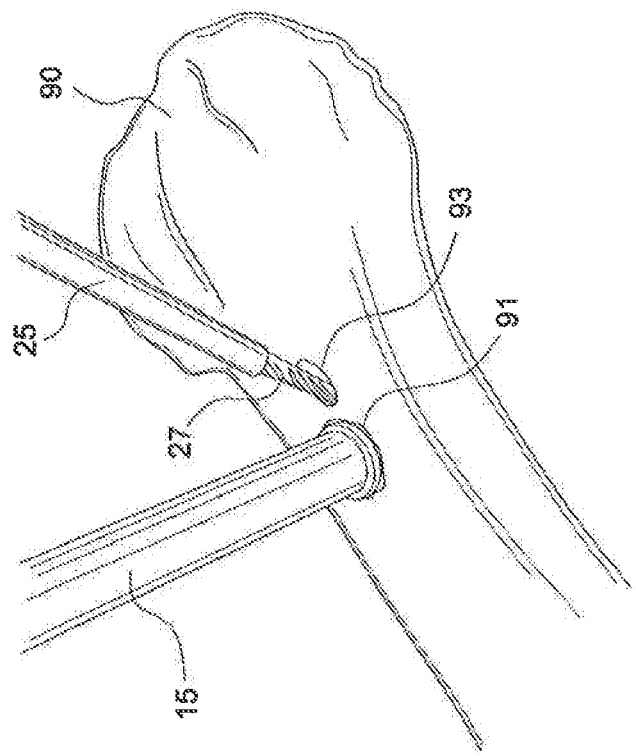
Figure 6:
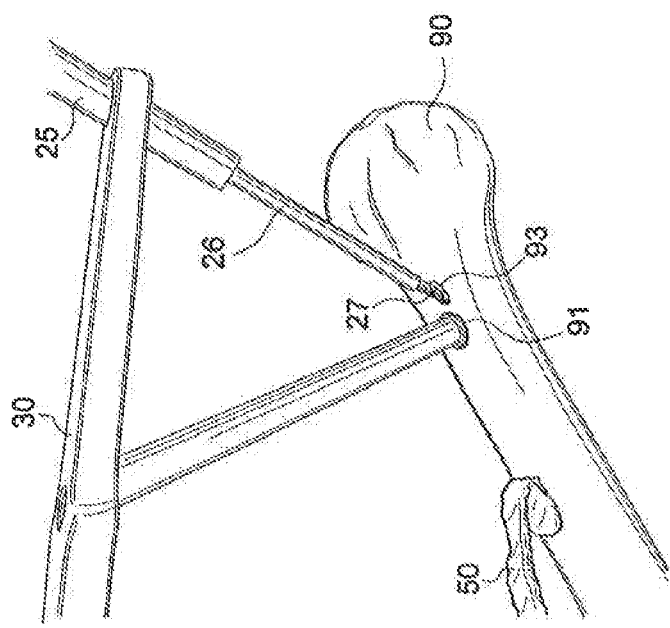

FIGS. 6 and 7: The drill 27 is inserted into the superior cannulated sleeve 26 and drilled into the bone 90 forming an intersection bone tunnel 93 to the previously formed unicortical bone socket 91. Because of the alignment of the inferior and superior tubes 15, 25, bone tunnel 93 intersects bone tunnel 91, i.e., the two bone tunnels form a resulting humeral intersecting structure having a V-shaped configuration.

FIG. 8: A flexible material 60, for example, a stiffened suture 60 such as Arthrex FiberStick™ or a PDS suture 60 is inserted into the superior cannulated sleeve 26 and pushed down till it seats into the tip of the inferior cannulated tube 15 within the bone socket 91.

Figure 9:
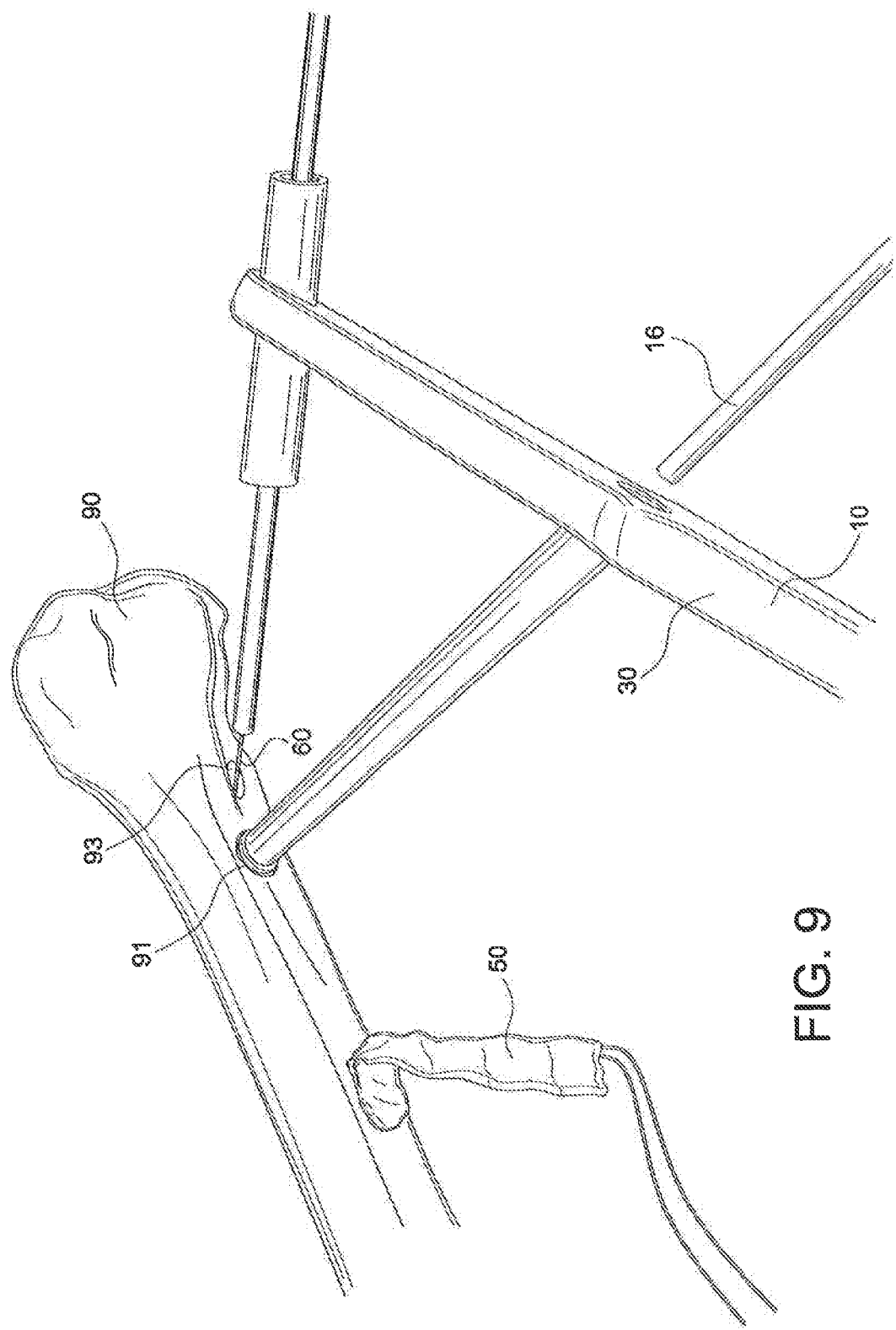

FIG. 9: The solid rod 16 is inserted into the inferior tube 15 of the triangular guide 10 and fully seated to capture the stiffened suture 60 (FiberStick™) or PDS suture 60.

Figure 10:
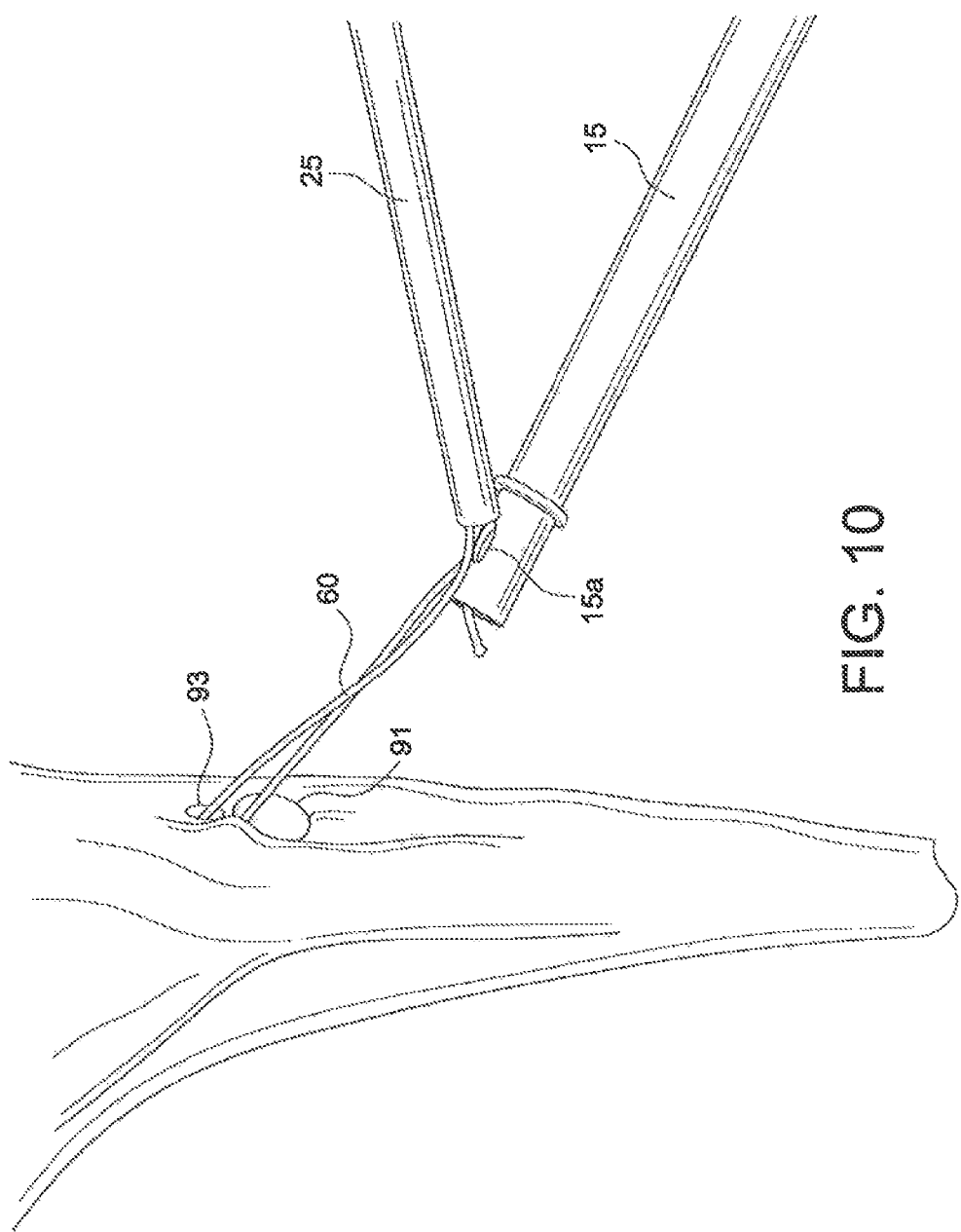

FIG. 10: The entire guide 10 is then removed with the captured stiffened suture 60 which will then be used to shuttle the locking stitch suture 51 placed in the biceps 50 (as detailed below).

Figure 11:
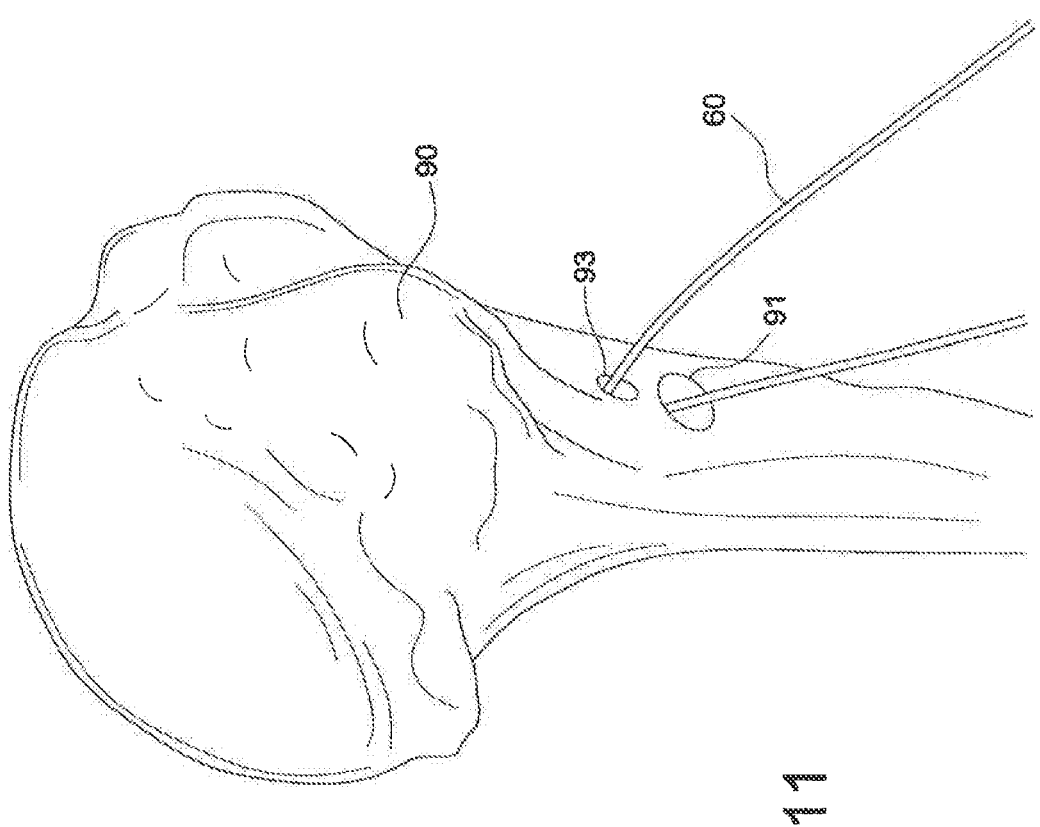

FIG. 11: The stiffened suture 60 has been passed through the intersecting bone tunnels 91, 93 which will then be used to shuttle the locking stitch suture 51 placed in the biceps 50 (as detailed below).

Figure 12:
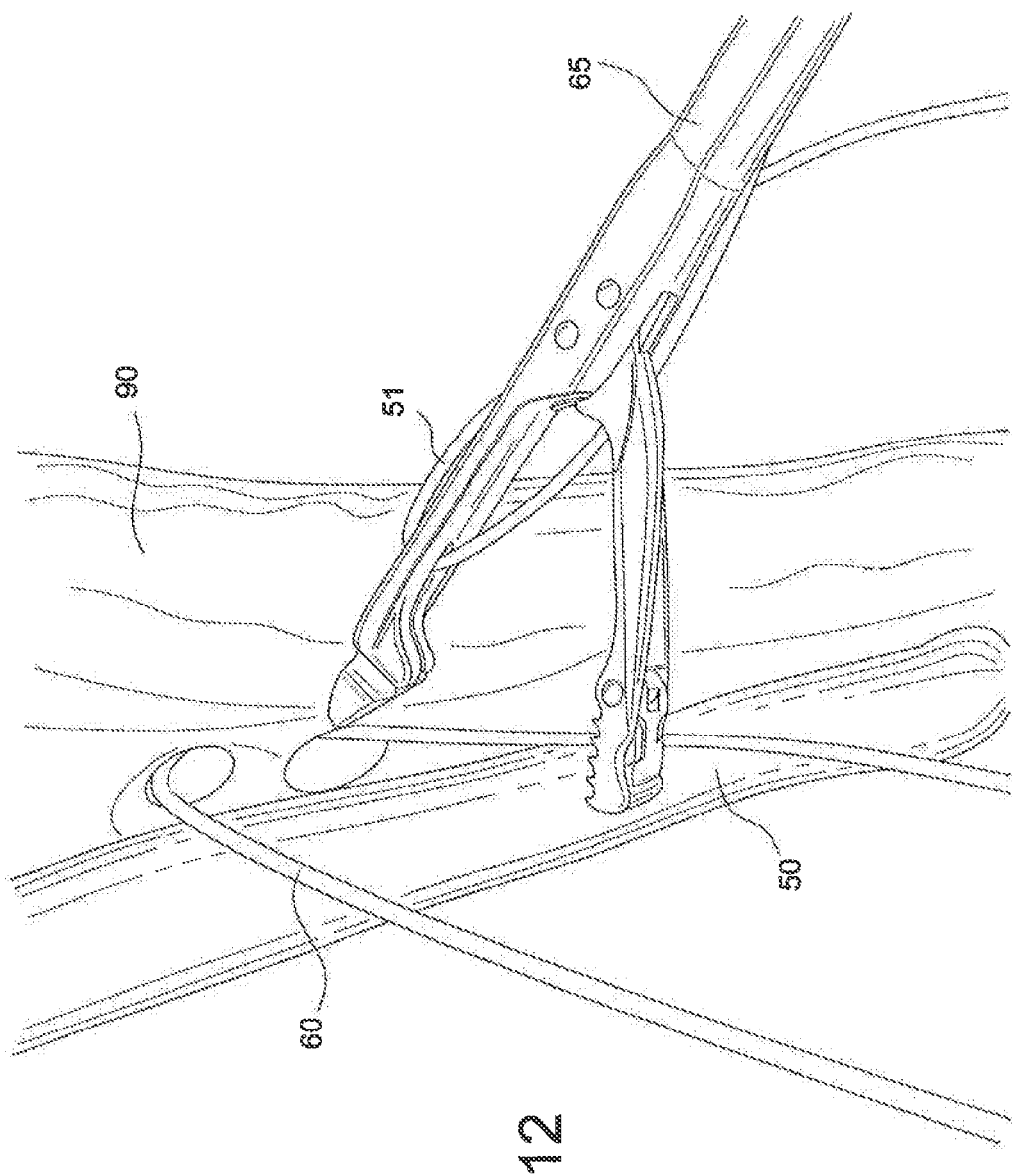

FIG. 12: A suture passing device 65 is then used to pass at least one flexible strand 51 (a free suture 51) through the biceps tendon 50 creating a stitch region 55 (a locking suture stitch 55).

Figure 13:
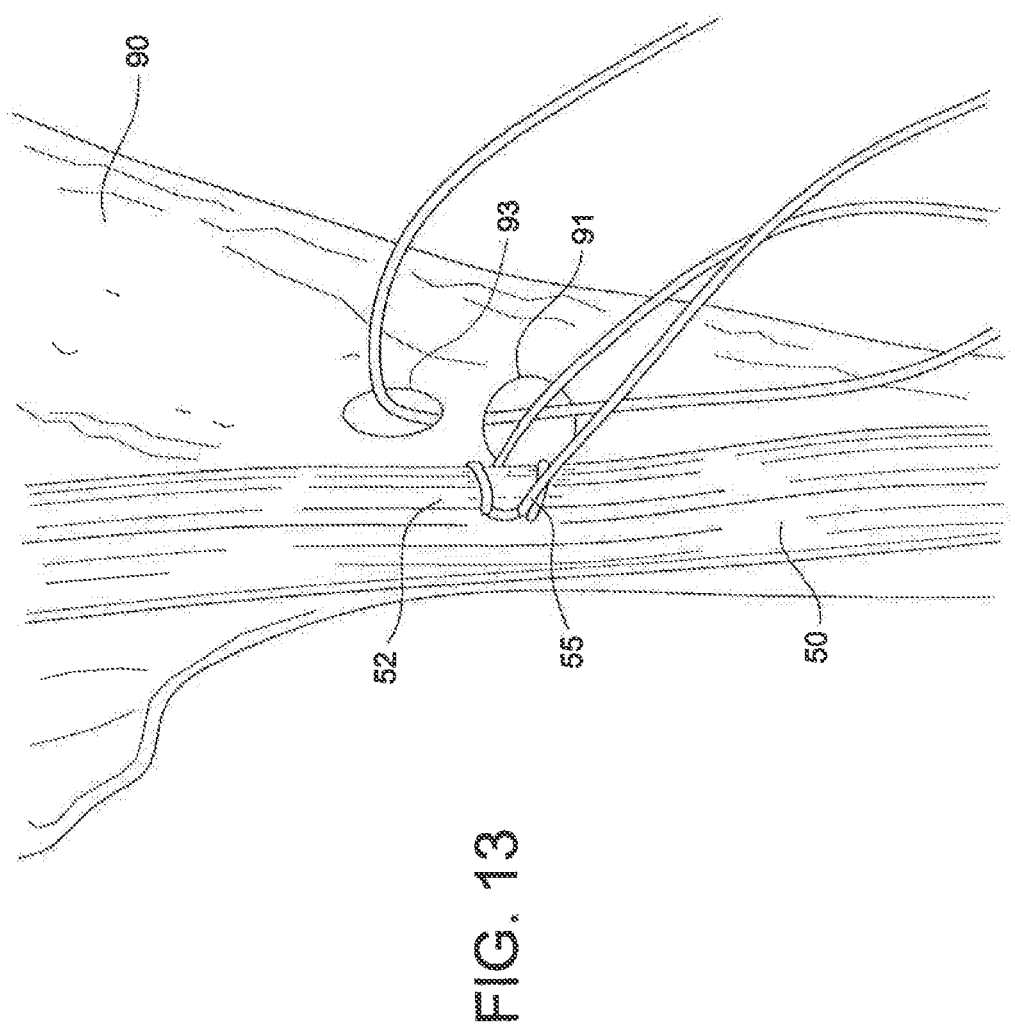

FIG. 13: Locking stitch 55 is formed in biceps tendon 50 (around the long head 52) at a position adjacent to the inferior bone socket 91.

Figure 14:
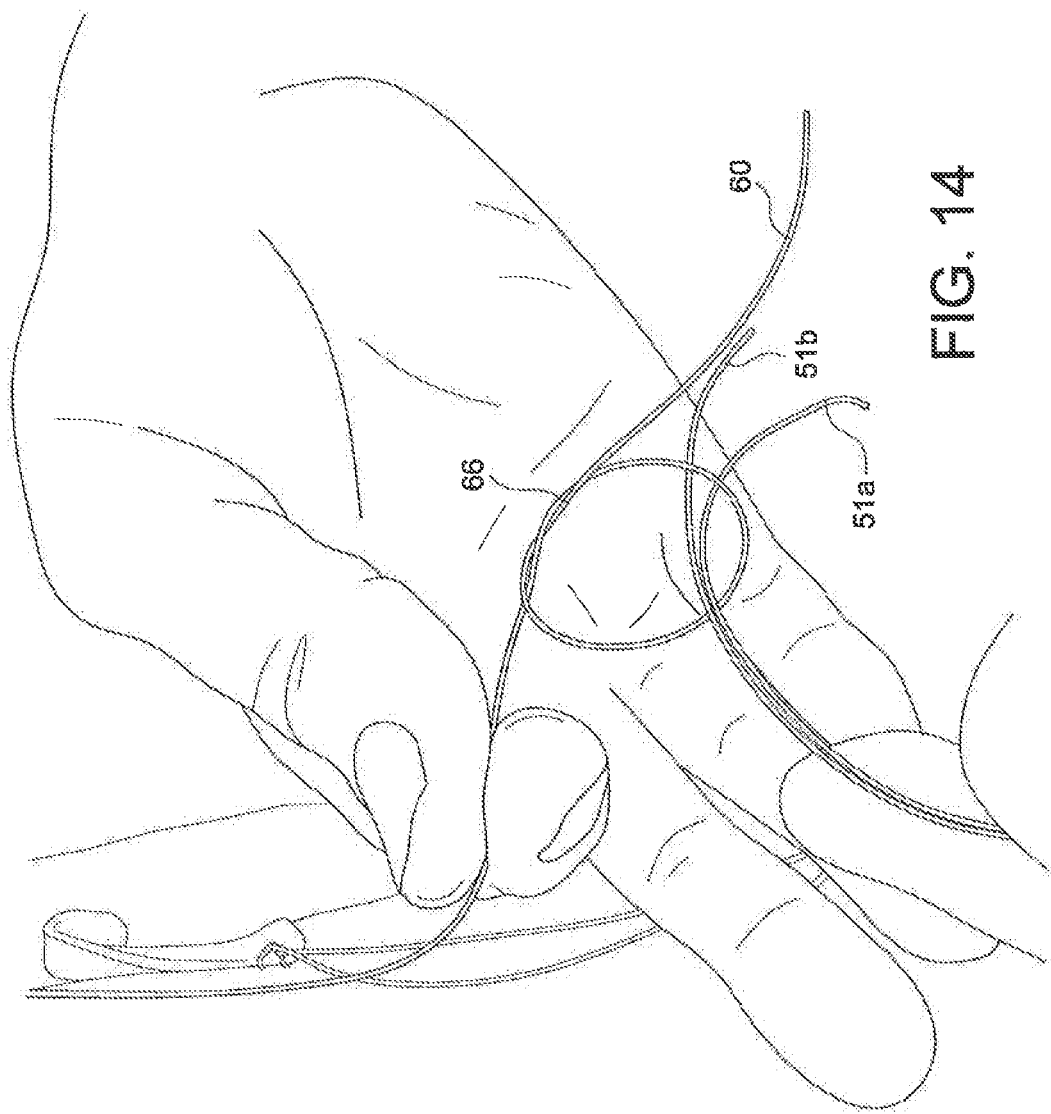

FIG. 14: A loop knot 66 is formed in the inferior tail of the stiffened suture 60 which was previously passed through the intersecting bone tunnel 91, 93. Both suture ends 51*a*, 51*b* from the suture 51 of locking stitch 55 passed through the biceps tendon 50 are placed within the loop knot 66 which is then tightened.

Figure 15:
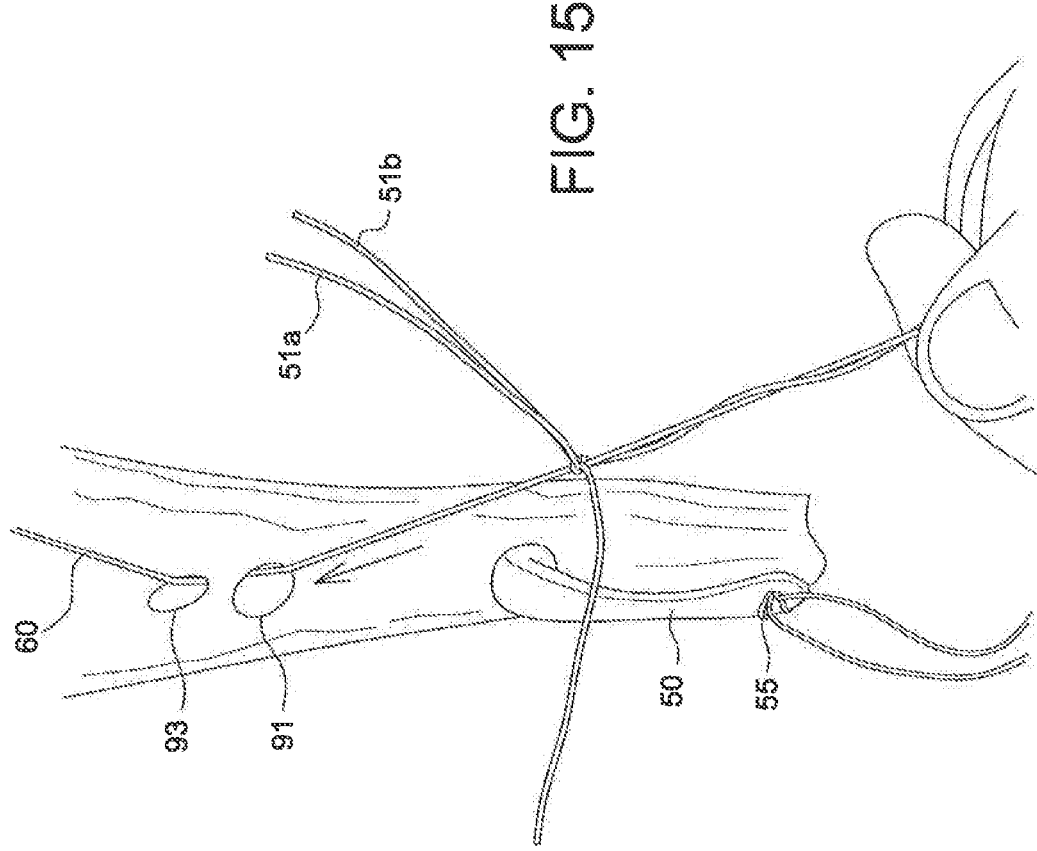

FIG. 15: The superior end of the suture shuttle is pulled to deliver the ends 51*a*, 51*b* of the locking stitch 55 that were previously placed in the biceps tendon 50.

Figure 16:
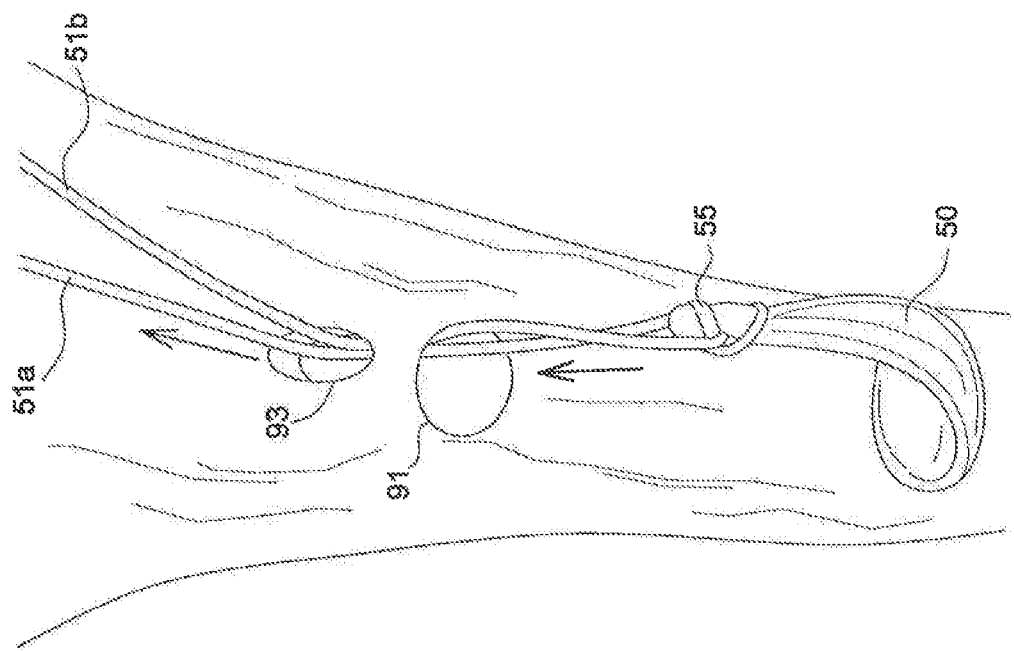

FIG. 16: The resected biceps 50 with locking stitch 55 is then delivered into the inferior bone socket 91 using a shuttle method.

Figure 17:
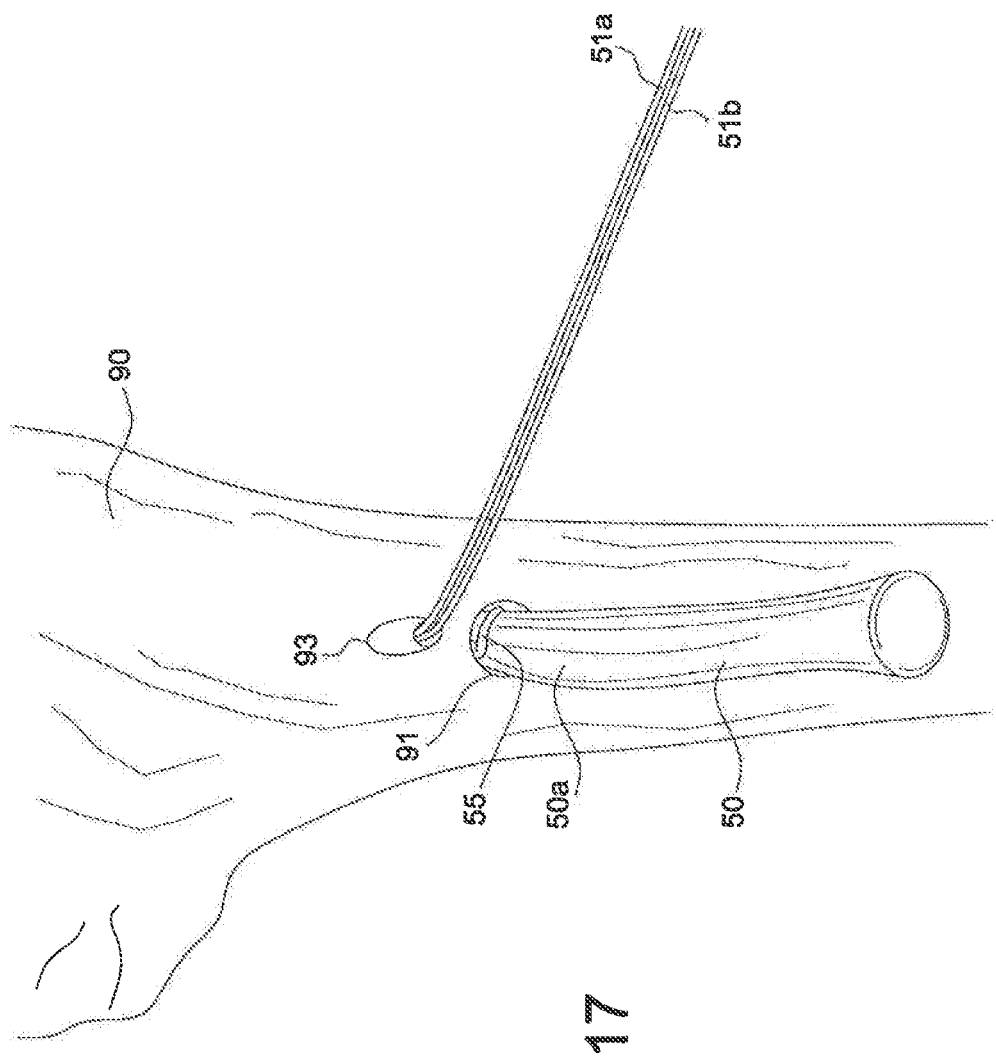

FIG. 17: The end 50*a* with locking stitch 55 of the biceps 50 is "docked" into the inferior bone socket 91 with the attached locking stitch ends exiting the superior bone tunnel 93.

Figure 18:
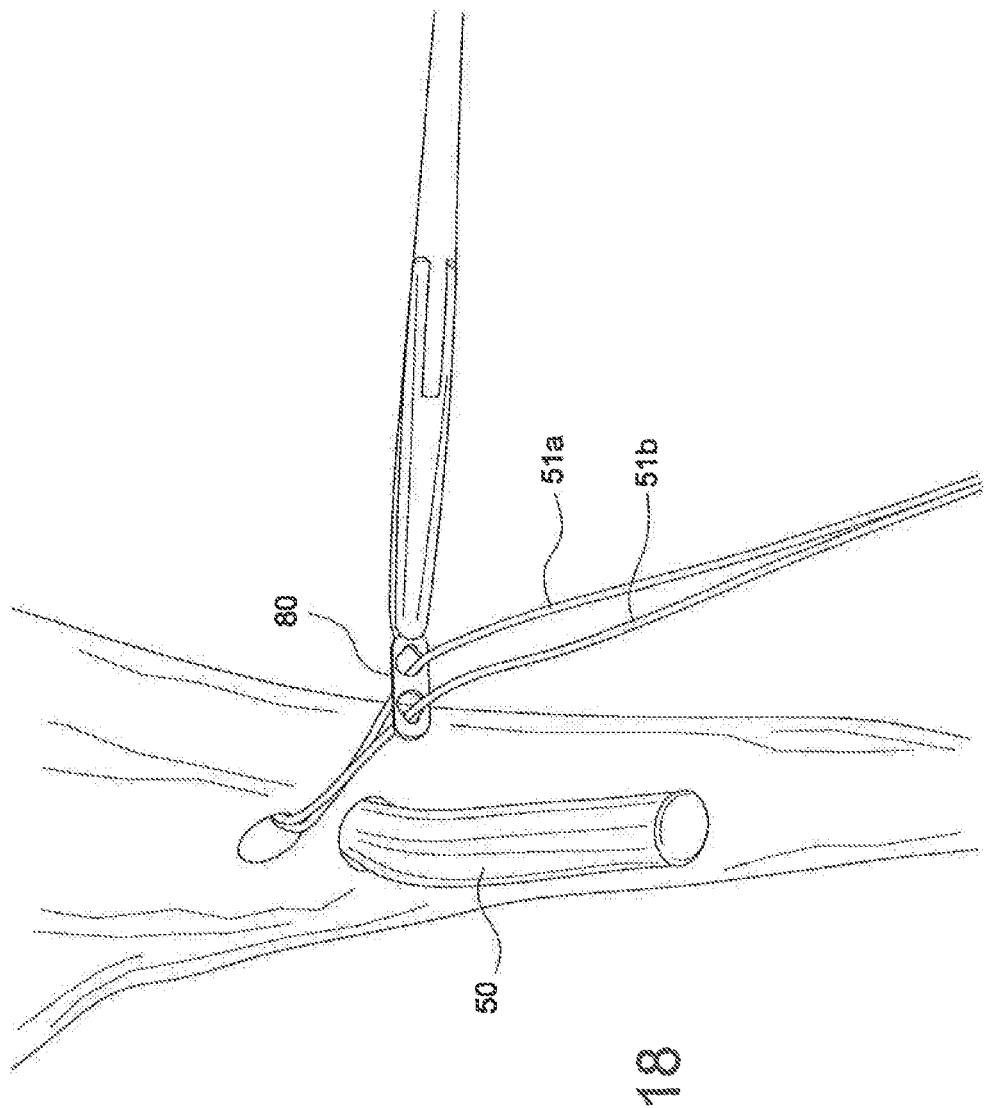

FIG. 18: The two suture ends 51*a*, 51*b* from the biceps locking stitch 55 are placed individually into a fixation device 80, for example, a button 80 (button implant 80 such as BicepsButton™ 80).

FIG. 19: The button implant 80 is secured against the proximal bone tunnel 93 with locking suture knots 88 formed by suture ends 51*a*, 51*b*, to achieve final repair 100.

During surgery, to obtain resected biceps 50 with locking stitch 55, the biceps tendon 50 (attached to an extremity of a patient and to humerus 90) may be first exposed and reflected away from the bicipital groove with a grasper instrument, for example. The long head of the biceps is identified. The native tendon biceps may be exposed without externalizing the native biceps.

Using suture passing instrument 65, such as a Scorpion Suture Passer, pass at least one flexible strand 51 (for example, suture such as a #2 FiberWire® suture) through at least a portion of the biceps 50 adjacent the bone socket 91 (i.e., in the immediate vicinity of the bone socket 91) to form stitched region 55 and tails, ends or limbs 51*a*, 51*b* of the at least one flexible strand 51. Biceps tendon 50 may be whipstitched arthroscopically with a suture passer instrument such as Arthrex Scorpion Suture Passer or similar instrument, to obtain stitched/whipstitched region 55 of the biceps tendon 50. The tendon may then be cut/resected above the stitched/whipstitched region 55.

As a result of the configuration of the drill guide system 30, the two bone sockets or tunnels 91, 93 are formed in a direction oblique to the bone, i.e., non-perpendicular to the humeral cortex, so that the two bone sockets or tunnels 91, 93 intersect within the bone 90 and form the resulting combined tunnel with a V shape.

The technique of the present invention restores the biceps anatomy to the humeral side, takes advantage of superior biomechanics, relies on bicortical fixation, and allows immediate postoperative range of motion.

A method of tendon repair of the present invention comprises the steps of: (i) forming a first bone socket and a second bone socket in a bone adjacent a native tendon, the native tendon being naturally attached to the bone, the first bone socket being spaced apart from the second bone socket at a cortical surface of the bone but intersecting with each other within the bone; (ii) passing a flexible strand around or through a region of the native tendon adjacent the first bone socket; and (iii) passing the flexible strand through the first bone socket, through the second bone socket and out of the second bone socket, to insert the native tendon into the first bone socket. The flexible strand may be secured on the bone cortex by button fixation, for example, or similar fixation techniques. The first bone socket may have a diameter greater than the diameter of the second bone socket.

An exemplary method of arthroscopic biceps tenodesis comprises inter alia the steps of: (i) forming a unicortical bone socket 91 at the inferior border of the bicipital groove on the proximal humerus; (ii) inserting a first cannulated tube 15 of a drill guide system 30 into the unicortical bone socket 91; (iii) with the first cannulated tube remaining in place, forming a second tunnel or socket 93 in the humerus with a second cannulated tube 25, a cannulated sleeve 26 and a drill 27, so that the second tunnel or socket 93 is spaced apart from the first tunnel or socket 91 and intersects the first tunnel 91 to form a resulting humeral intersecting structure, the first and second cannulated tubes being non-parallel relative to each other, to allow the resulting humeral intersecting structure to have a V-shaped configuration; (iv) attaching at least one flexible strand 51 to a biceps tendon 50 at a region adjacent the unicortical bone socket 91; (v) passing the at least one flexible strand 51 through both the first and second sockets 91, 93 to insert the biceps tendon into the first socket; and (vi) securing the at least one flexible strand 51 to a fixation device 80 (for example, a button 80) onto the humeral cortex.

The surgical repairs of the present invention may employ any type of flexible material or suture 60, 51, for example FiberWire® or FiberTape® or FiberChain®. Flexible strand or cord 60, 51 may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strand 51 may be also in the form of flat suture tape (for example, a collagen stuffed suture tape or a high strength suture tape, such as disclosed in U.S. Pat. No. 7,892,256) or a combination of suture and tape, a stiff material, or combination of stiff and flexible materials, depending on the intended application. The flexible strand 51 may be also in the form of a suture chain described in U.S. Pat. No. 7,803,173 and/or in U.S. Patent Appl. Publ. No. 2007/0135843, the disclosures of both of which are incorporated by reference in their entirety herewith. The strands 51 may also be formed of a stiff material, or combination of stiff and flexible materials, depending on the intended application. The strands may be also coated and/or provided in different colors.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

The invention claimed is:

1. A method of tendon repair, comprising:
   forming a first bone socket and a second bone socket in a bone adjacent to a native tendon, the native tendon being naturally attached to the bone, the first bone socket being spaced apart from the second bone socket at a cortical surface of the bone but intersecting with the second bone socket within the bone, wherein the second bone socket is superior to the first bone socket, and further wherein both the first bone socket and the second bone socket are formed at a location of the bone that is inferior to a greater tuberosity of the bone;
   passing a flexible strand around or through a region of the native tendon adjacent the first bone socket;
   passing the flexible strand through the first bone socket, through the second bone socket, and then out of the second bone socket, to insert the native tendon into the first bone socket; and
   securing the flexible strand at the cortical surface of the bone with a fixation device that is positioned over the second bone socket.

2. The method as recited in claim 1, comprising:
   inserting a first cannulated tube of a triangular guide into the first bone socket, the triangular guide including a plate, the first cannulated tube, and a second cannulated tube, the first and second cannulated tubes being non-parallel to each other and relative to the plate; and
   forming the second bone socket with the second cannulated tube and a drill, the second bone socket intersecting the first bone socket and forming a resulting bone tunnel having a V shape.

3. The method as recited in claim 2, comprising:
   passing tails of the flexible strand through the second bone socket of the resulting bone tunnel with the V shape; and
   securing the tails of the flexible strand to the fixation device onto the cortical surface of the bone and over the second bone socket.

4. The method as recited in claim 3, comprising tying the tails of the flexible strand over the fixation device.

5. The method as recited in claim 3, comprising attaching the tails of the flexible strand to a suture passer and passing the tails through and out of the second bone socket.

6. The method as recited in claim 5, wherein the suture passer is a loop of a stiffened suture.

7. The method as recited in claim 5, wherein the suture passer is a nitinol loop.

8. The method as recited in claim 1, wherein the fixation device is a button.

9. The method as recited in claim 1, wherein the first bone socket has a diameter larger than a diameter of the second bone socket.

10. The method as recited in claim 1, wherein the native tendon is a biceps tendon.

11. The method as recited in claim 1, wherein the flexible strand is a suture, a suture tape, or a suture chain.

12. The method as recited in claim 1, wherein the flexible strand is formed of a suture material comprising ultrahigh molecular weight polyethylene.

13. The method as recited in claim 1, wherein the first bone socket is inferior to the second bone socket.

14. The method as recited in claim 1, wherein passing the flexible strand around or through the region of the native tendon includes forming a locking stitch in the region, and further wherein the region of the native tendon with the locking stitch is docked inside the first bone socket once the flexible strand has been passed through the first bone socket, through the second bone socket, and then out of the second bone socket.

15. The method as recited in claim 1, wherein the first bone socket is an inferior humeral bone socket and the second bone socket is a superior humeral bone socket.

16. The method as recited in claim 1, wherein the first bone socket and the second bone socket are non-perpendicular to one another.

17. The method as recited in claim 1, wherein the first bone socket and the second bone socket are formed on a common side of the bone.

18. The method as recited in claim 1, wherein the first bone socket is formed at an inferior border of a bicepital groove.

19. The method as recited in claim 1, wherein the bone is a humerus and the native tendon is a biceps tendon, and further wherein each of the first bone socket and the second bone socket is formed in a shaft of the humerus.

20. A method of tendon repair, comprising:
   forming a first bone socket in a bone at a location adjacent to a native tendon;
   forming a second bone socket in the bone at a superior location relative to the first bone socket, the first bone socket being spaced apart from the second bone socket at a cortical surface of the bone but intersecting with the second bone socket inside the bone,
   wherein both the first bone socket and the second bone socket are formed at a position of the bone that is inferior to a greater tuberosity of the bone;
   passing a flexible strand around or through a region of the native tendon that is adjacent to the first bone socket;
   passing the flexible strand through the first bone socket, then through the second bone socket, and then out of the second bone socket, thereby positioning a portion of the native tendon inside the first bone socket; and
   securing the flexible strand at the cortical surface of the bone with a button fixation device that is positioned over the second bone socket.

\* \* \* \* \*